(12) United States Patent
Koenig et al.

(10) Patent No.: US 11,842,030 B2
(45) Date of Patent: Dec. 12, 2023

(54) METHOD AND APPARATUS FOR IMAGE-BASED NAVIGATION

(71) Applicant: Medtronic Navigation, Inc., Louisville, CO (US)

(72) Inventors: Matthew W. Koenig, Denver, CO (US); Michael E. Alley, Morrison, CO (US); Jennifer L. Halcome, Longmont, CO (US); Joseph S. Johnson, III, Firestone, CO (US); Lavie P. Golenberg, Edina, MN (US)

(73) Assignee: Medtronic Navigation, Inc., Louisville, CO (US)

( * ) Notice: Subject to any disclaimer, the term of this patent is extended or adjusted under 35 U.S.C. 154(b) by 299 days.

(21) Appl. No.: 15/420,831

(22) Filed: Jan. 31, 2017

(65) Prior Publication Data
US 2018/0217734 A1    Aug. 2, 2018

(51) Int. Cl.
*G06F 3/04817* (2022.01)
*A61B 34/10* (2016.01)
(Continued)

(52) U.S. Cl.
CPC .......... *G06F 3/04817* (2013.01); *A61B 34/10* (2016.02); *A61B 34/20* (2016.02); *A61B 34/25* (2016.02); *G06T 7/0012* (2013.01); *G06T 11/60* (2013.01); *A61B 90/10* (2016.02); *A61B 90/11* (2016.02); *A61B 2034/107* (2016.02); *A61B 2034/2051* (2016.02);
(Continued)

(58) Field of Classification Search
CPC .............. A61B 34/20; A61B 34/25; A61B 2034/2046–2074; A61B 2034/252–258; A61B 90/10–18; A61B 2090/101–103; A61B 2034/107; A61B 34/10; A61B 2034/101–108; G06F 3/048; G06F 3/04817; G06T 7/0012–0016; G06T 11/60; G06T 2200/24; G06T 2207/30096
See application file for complete search history.

(56) References Cited

U.S. PATENT DOCUMENTS 5,592,939 A    1/1997    Martinelli
5,913,820 A    6/1999    Bladen et al.
(Continued)

FOREIGN PATENT DOCUMENTS

CN    101918855 A    12/2010
CN    110461265 A    11/2019
(Continued)

OTHER PUBLICATIONS

"Zimmer® PSI Shoulder for Trabecular Metal™ Reverse Glenoid Online Preoperative Planning Session." Zimmer Biomet (Year: 2013).*
(Continued)

*Primary Examiner* — Liang Y Li
(74) *Attorney, Agent, or Firm* — Harness, Dickey & Pierce, P.L.C.

(57) ABSTRACT

A system and method for a procedure that can be performed on an appropriate subject. A procedure may be planned, at least in part, prior to performing the procedure. An image may illustrate at least a portion of the planned procedure for confirmation and/or alteration of the planned procedure prior to performing the procedure.

16 Claims, 7 Drawing Sheets

(51) Int. Cl.
*A61B 34/00* (2016.01)
*A61B 34/20* (2016.01)
*A61B 90/10* (2016.01)
*A61B 90/11* (2016.01)
*G06T 7/00* (2017.01)
*G06T 11/60* (2006.01)

(52) U.S. Cl.
CPC .......... *A61B 2034/2055* (2016.02); *A61B 2034/2063* (2016.02); *A61B 2034/2072* (2016.02); *G06T 2200/24* (2013.01); *G06T 2207/30096* (2013.01)

(56) References Cited

U.S. PATENT DOCUMENTS

| | | | |
|---|---|---|---|
| 5,983,126 A | 11/1999 | Wittkampf | |
| 6,235,038 B1 | 5/2001 | Hunter et al. | |
| 6,240,308 B1 | 5/2001 | Hardy et al. | |
| 6,474,341 B1 | 11/2002 | Hunter et al. | |
| 6,546,277 B1 | 4/2003 | Franck et al. | |
| 6,636,757 B1 | 10/2003 | Jascob et al. | |
| 6,747,539 B1 | 6/2004 | Martinelli | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,636,596 B2 | 12/2009 | Solar | |
| 7,637,915 B2 | 12/2009 | Parmer et al. | |
| 7,658,879 B2 | 2/2010 | Solar | |
| 7,695,480 B2 | 4/2010 | Solar et al. | |
| 7,699,854 B2 | 4/2010 | Mazzocchi et al. | |
| 7,751,865 B2 | 7/2010 | Jascob et al. | |
| 7,797,032 B2 | 9/2010 | Martinelli et al. | |
| 7,896,889 B2 | 3/2011 | Mazzocchi et al. | |
| 7,981,120 B2 | 7/2011 | Mazzocchi et al. | |
| 8,010,177 B2 | 8/2011 | Csavoy et al. | |
| 8,116,850 B2 | 2/2012 | Solar | |
| 8,301,226 B2 | 10/2012 | Csavoy et al. | |
| 8,617,180 B2 | 12/2013 | Thiran et al. | |
| 8,644,907 B2 | 2/2014 | Hartmann et al. | |
| 8,831,307 B2 | 9/2014 | Cagnan et al. | |
| 8,911,452 B2 | 12/2014 | Skakoon et al. | |
| 8,942,446 B2 | 1/2015 | Martens | |
| 9,002,076 B2 | 4/2015 | Khadem et al. | |
| 9,008,414 B2 | 4/2015 | Merkl et al. | |
| 9,222,996 B2* | 12/2015 | Fujimoto | G01R 33/286 |
| 9,265,523 B2 | 2/2016 | Mark et al. | |
| 10,413,366 B2* | 9/2019 | Dyer | G16H 40/63 |
| 10,729,499 B2* | 8/2020 | Liu | A61B 34/10 |
| 10,918,413 B2* | 2/2021 | Hazard, III | A61B 34/20 |
| 2003/0184577 A1* | 10/2003 | Petrella | G16H 70/00 715/719 |
| 2003/0187351 A1 | 10/2003 | Franck et al. | |
| 2006/0189842 A1 | 8/2006 | Hoeg et al. | |
| 2008/0097187 A1 | 4/2008 | Gielen et al. | |
| 2009/0124896 A1 | 5/2009 | Haras | |
| 2009/0259230 A1 | 10/2009 | Khadem et al. | |
| 2010/0228117 A1 | 9/2010 | Hartmann | |
| 2014/0199072 A1 | 7/2014 | Nuijts et al. | |
| 2014/0201669 A1 | 7/2014 | Liu et al. | |
| 2015/0283379 A1 | 10/2015 | Venkatesan | |
| 2015/0359597 A1* | 12/2015 | Gombert | B25J 9/0087 901/8 |
| 2016/0067007 A1 | 3/2016 | Piron et al. | |
| 2016/0070436 A1* | 3/2016 | Thomas | A61B 6/032 715/771 |
| 2016/0135816 A1* | 5/2016 | Lavallee | A61B 17/17 606/88 |
| 2016/0196650 A1 | 7/2016 | Ekin et al. | |
| 2017/0000562 A1* | 1/2017 | Frank | A61B 17/8061 |
| 2017/0000581 A1* | 1/2017 | Tokuda | G06K 9/6218 |
| 2017/0071672 A1* | 3/2017 | Shochat | G06T 7/11 |
| 2022/0211270 A1* | 7/2022 | Itkowtiz | A61B 5/0013 |

FOREIGN PATENT DOCUMENTS

| | | |
|---|---|---|
| JP | 2016517288 A | 6/2016 |
| JP | 2017528175 A | 9/2017 |
| WO | 0019927 | 4/2000 |
| WO | 2015132787 A1 | 9/2015 |

OTHER PUBLICATIONS

Konrad, Peter, et al. Customized, Miniature Rapid-Prototype Stereotactic Frames for Use in Deep Brain Stimulator Surgery: Initial Clinical Methodology and Experience from 263 Patients from 2002 to 2008. Dec. 15, 2010. Stereotactic and Functional Neurosurgery. 2011:89, 34-41. (Year: 2010).*
Hata, Nobuhiko, et al. "Body-mounted robotic instrument guide for image-guided cryotherapy of renal cancer." Medical physics 43.2 (2016): 843-853. (Year: 2016).*
Medtronic "Cranial Navigation: A Brain Biopsy Solution Built Around Your Surgical Workflow" biopsy sales sheet, 2 pages, 2013.
Nexframe Procedure, Cone of Reachability, pp. 63-66, Dec. 6, 2016.
Hess Maggie et al., "Visual design and verification tool for collision-free dexterous patient specific neurosurgical instruments", Progress in Biomedical Optics and Imaging, SPIE—International Society for Optical Engineering, Bellingham, WA, US, vol. 9786, Mar. 18, 2016 (Mar. 18, 2016), p. 97861M-97861M, XP060069347.
International Preliminary Report On Patentability regarding International Application No. PCT/US2018/015970, dated Aug. 15, 2019.
Junichi Tokuda et al, "Preclinical evaluation of an MRI-compatible pneumatic robot for angulated needle placement in transperineal prostate interventions", International Journal of Computer Assisted Radiology and Surgery; A Journal for Interdisciplinary Research, Development and Applications of Image Guided Diagnosis and Therapy, Springer, Berlin, DE,vol. 7, No. 6, Jun. 8, 2012 (Jun. 8, 2012), p. 949-957, XP035132555.
Japanese Office Action (with English translation) regarding Application No. 2019541190, dated Oct. 21, 2021.
Hess, Maggie, et al. "Visual design and verification tool for collision-free dexterous patient specific neurosurgical instruments." Medical Imaging 2016: Image-Guided Procedures, Robotic Interventions, and Modeling. vol. 9786. SPIE, 2016.
Korean Office Action regarding Application No. 102019702467.7, dated Feb. 4, 2022.
Chinese Office Action regarding Patent Application No. 201880020846.8, dated Apr. 6, 2022.
"Visual design and verification tool forcollision-free dexterous patientspecific neurosurgical instruments", Hess et al., Proceedings of SPIE, vol. 9786; pp. 97861M-1-97861M-18.
International Search Report and Written Opinion regarding International Application No. PCT/US2018/015970, dated May 16, 2018.
European Patent Office Communication corresponding to EP Application No. 18706892.9, dated Oct. 7, 2022.

* cited by examiner

METHOD AND APPARATUS FOR IMAGE-BASED NAVIGATION

FIELD

The subject disclosure relates to a system for planning and/or performing a procedure, and exemplarily relates to a system to use imaging of a subject for planning and selecting a procedure for on a subject.

BACKGROUND

This section provides background information related to the present disclosure which is not necessarily prior art.

The images of a subject may be acquired prior to a procedure and intra- or post-operatively or post-procedurally. For example, image data can be acquired of a patient and a three-dimensional model of the subject can be generated based upon the acquired image data. The three-dimensional model can be used for various purposes, such as planning a procedure on the subject including selecting an implant (if an implant is to be positioned in the subject), determining entry points, and/or trajectories for performing a procedure and/or implantation, and other selected planning features. Further, the planning can include determining placement of a selected implant, such as a lead electrode for a cardiac system (e.g., a cardiac synchronization system) or a lead for a brain stimulation system.

SUMMARY

This section provides a general summary of the disclosure, and is not a comprehensive disclosure of its full scope or all of its features.

A system and/or method is/are disclosed that may be used to plan a trajectory and/or placement of an instrument. The planning may be for placing an implant and/or positioning an instrument temporarily. For example, planning may include selecting a trajectory for placing a deep brain stimulation (DBS) probe in a subject, positioning a fastener within an enclosed structure of a subject, or other procedure. Similarly, planning may occur for performing a tumor biopsy, removal of an obstruction, or the like.

Often, prior to a procedure, planning may be performed for the procedure. The planning may include various steps, such as selecting an entry point, selecting a target, and selecting a trajectory to reach the target. The trajectory may generally include a direction and type of motion to move an instrument from the entry point to the target. The entry point may include an area or volume within an entry portal or passage through which the instrument may move, wherein the instrument includes a smaller dimension than the entire possible area of the entry portal. Therefore, an entry point may be smaller than an entry portal.

When planning a procedure, the user may review a map, including an image, of the subject prior to performing the procedure. The image or map of the subject may illustrate locations of various features, such as a target for a procedure. Further, the map or image data may illustrate or be used to determine a possible entry point. In addition to features or portions of the subject that may be illustrated with the map, a display device may be used to illustrate limitations and boundaries relevant to the selected procedure. For example, a guide instrument may have a size and range of motion to guide an instrument for a procedure. The extent of the range of motion may be illustrated on the image or map to assist in planning, including finalizing or selecting, a trajectory, guide, and other portions of a procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
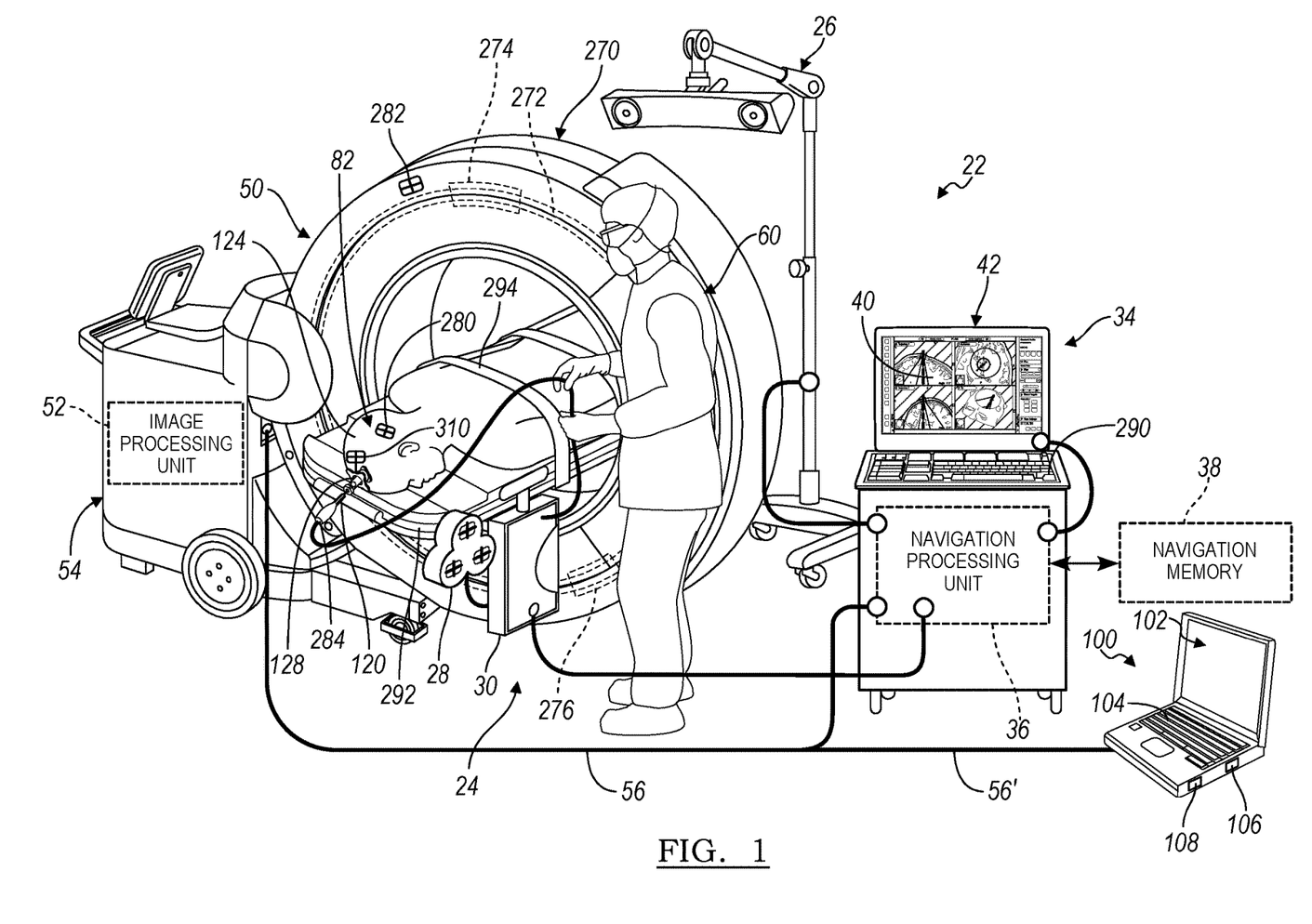
FIG. 1 is an environmental view of a plurality of systems that may be present in an operating theatre and/or used prior to a procedure, including an optional imaging system and a navigation system.

With initial reference to FIG. 1, a suite or assembly of systems 20 may be provided for a selected procedure. The systems may include instruments, processing systems, and the like may be included. In various embodiments, the suite 20 may include a navigation system 22 that may include one or more tracking systems 24, such as an optical tracking system including an optical localizer 26 and an electromagnetic tracking system including an electromagnetic tracking localizer 28. The tracking systems 24 may communicate with various instruments, as discussed herein, via a coil array controller/navigated instrument interface (CAC/NII) 30. The CAC/NII 30 may communicate with a workstation or other processing system or assembly 34. The navigation processor system 34 may include a navigation processing unit 36 that is configured and operable to access one or more navigation memory systems 38. The navigation memory system 38 may include a non-transitory memory that may include various features or programs stored for various procedures, such as instructions for determining a position (including location and orientation) of a tracked instrument, illustrating or super-imposing an icon on an image 40 that is displayed on a display device 42, or other appropriate instructions or program features, as discussed further herein.

The suite 20 may further include an imaging system 50, as discussed further herein. The imaging system 50 may include an imaging processing unit 52 that is incorporated with the imaging system 50, such as included or housed within a cart 54 and/or may be accessed remotely from the imaging system 50. The imaging processing unit 52 may process image data and transmit it to the navigation processing unit 36 via a transmission system 56 including wireless, wired, physical memory transfer, or the like. The image data acquired by the imaging system 50 may be used to generate the image 40 illustrated on the display device 42. It is understood that any appropriate imaging system may be included as the imaging system 50. The imaging system 50, specifically illustrated in FIG. 1, may include the O-arm® imaging system sold by Medtronic, Inc., having a place of business in Louisville, Colorado, but may also include or alternatively include other imaging systems such as computer tomography (CT) imaging systems, magnetic resonance imaging (MRI) systems, C-arm fluoroscopy imaging systems, etc.

Figure 5:
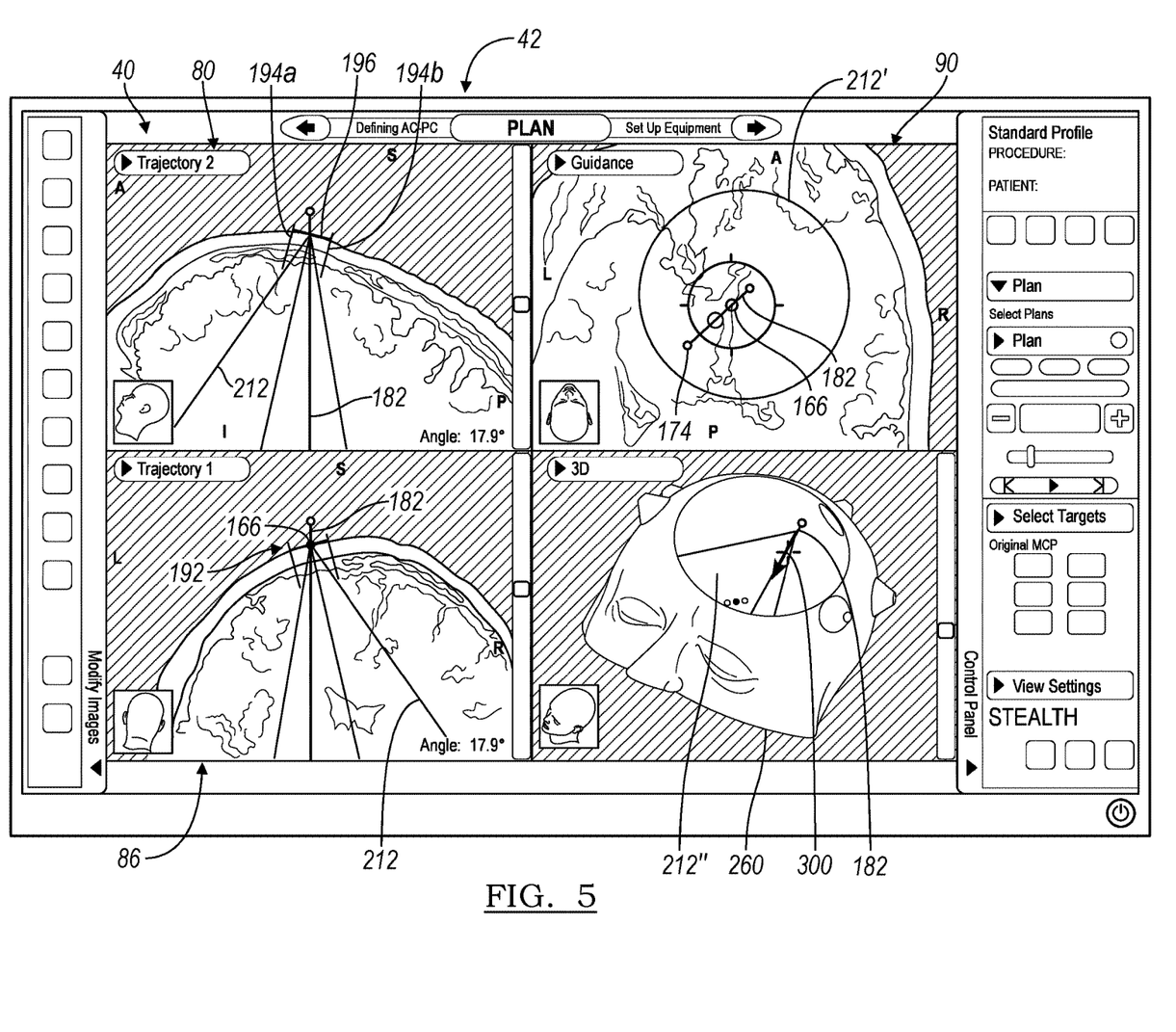
FIG. 5 is a screen shot of a display device illustrating various images and information regarding a plan for a procedure on the subject.

Image data may be acquired with any appropriate imaging system and may be used to generate the image 40 for display on the display device 42. It is understood that any appropriate type or number of images may be generated to be displayed on the display device 42. For example, the image 40 may include a plurality of images along with various software features or buttons, as illustrated in FIG. 5. The images may also include a plurality of separate or discreet images that may be individually viewed or selectively viewed by a user 60.

In addition to or alternatively to the navigation system 34, a planning system 100 may be used to display and/or manipulate the image data, as discussed herein. The planning system 100 may be used to assist in or perform planning of a selected procedure, such as by displaying icons on a display device 102 that displays the images. The image data acquired with the selected imaging system 50 may be used to generate an image for viewing on a selected display device, such as the display device 40 and/or 102. In various embodiments, the user 60 may use the image data acquired with the imaging system 50 to generate or determine a plan prior to performing any portion of a procedure, such as forming a burr hole, an instrument, removing an access panel from a non-living subject, or the like. It is understood that any access portal, such as any appropriate craniotomy, may be used in a selected procedure, and a burr hole is merely exemplary. In various embodiments, the planning system 100 may receive image data from the imaging device 50 for display on a display device, such as the monitor 102. The planning system 100 may further include various user inputs, such as a keyboard 104 or other appropriate user inputs such as a track pad, mouse, or the like.

The planning system 100 may further include a planning processor system 106, similar to the processor system 36 discussed herein. Further, the planning system 100 may include a planning memory 108 similar to the navigation memory 38 discussed herein. The planning processor system 106 of the planning system 100 may be able to execute various instructions, such as stored in the memory 108 to assist in planning a selected procedure on the subject 82. Further, the memory 108 may have written thereto a plan that is determined for performing the procedure. As discussed herein, the planning system 100 may be used to determine a plan for performing a procedure. The plan may be made prior to a procedure and may be stored to the memory 108. Thus, the plan may be predetermined prior to performing the procedure.

In various embodiments, including a specific example discussed herein, an instrument 120 may be planned to be positioned into a cranium 124 of the subject 82. The instrument 120 may be positioned or guided into the subject 82 through a selected guide system 128. The guide system 128 may be positioned relative to the cranium 124 of the subject 82, such as fixed to the cranium 124 and surrounding or positioned within a burr hole formed in the cranium 124. The guide system 128 may include selected or appropriate guide systems including those disclosed in U.S. Pat. Nos. 7,637,915; 8,301,226; or 7,695,480, all incorporated herein by reference. The guide system 128 may further include the Navigus® guide device and/or the Nexframe® guide device, both sold by Medtronic Navigation, Inc. having a place of business in Louisville, Colorado. It is understood, however, that the guide system 128 may be any appropriate guide that may be used to guide any selected instrument, such as the instrument 124 into the subject 82. The guide system 128 may include various guiding dimensions and geometries that may be selected or fixed by the guide that are predetermined and may be illustrated for planning and selecting a device, such as the guide 128 as discussed further herein.

Turning reference to FIG. 2, FIG. 3, FIG. 4, and FIG. 5, various image views are illustrated. It is understood that the image views, as discussed herein, may be viewed with the planning system 100 on the display device 102, such as during planning prior to any procedure occurring and/or with the navigation system 34 on the display device 42 during a procedure. Thus, a predetermined or pre-planned plan may be made and saved, such as in the memory 10, for recall at a later time. For example, the navigation system 34 may recall the pre-plan for display on the display device 42. Also, the user 60 may alter the pre-plan during a procedure for various purposes (e.g. brain shift, further development of a disease state, etc.).

Figure 2:
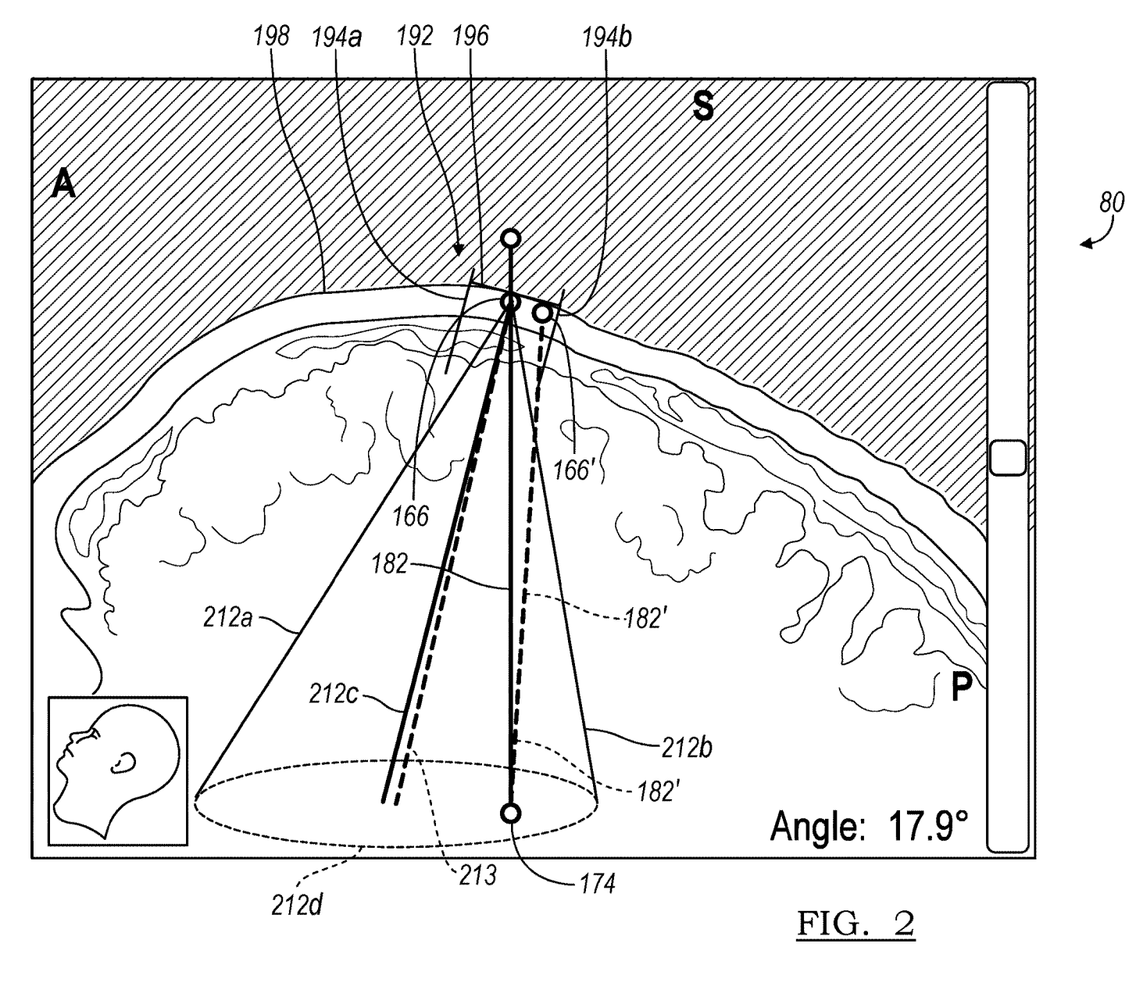
FIG. 2 is a first image based on image data acquired of a subject, according to various embodiments.
Figure 3:
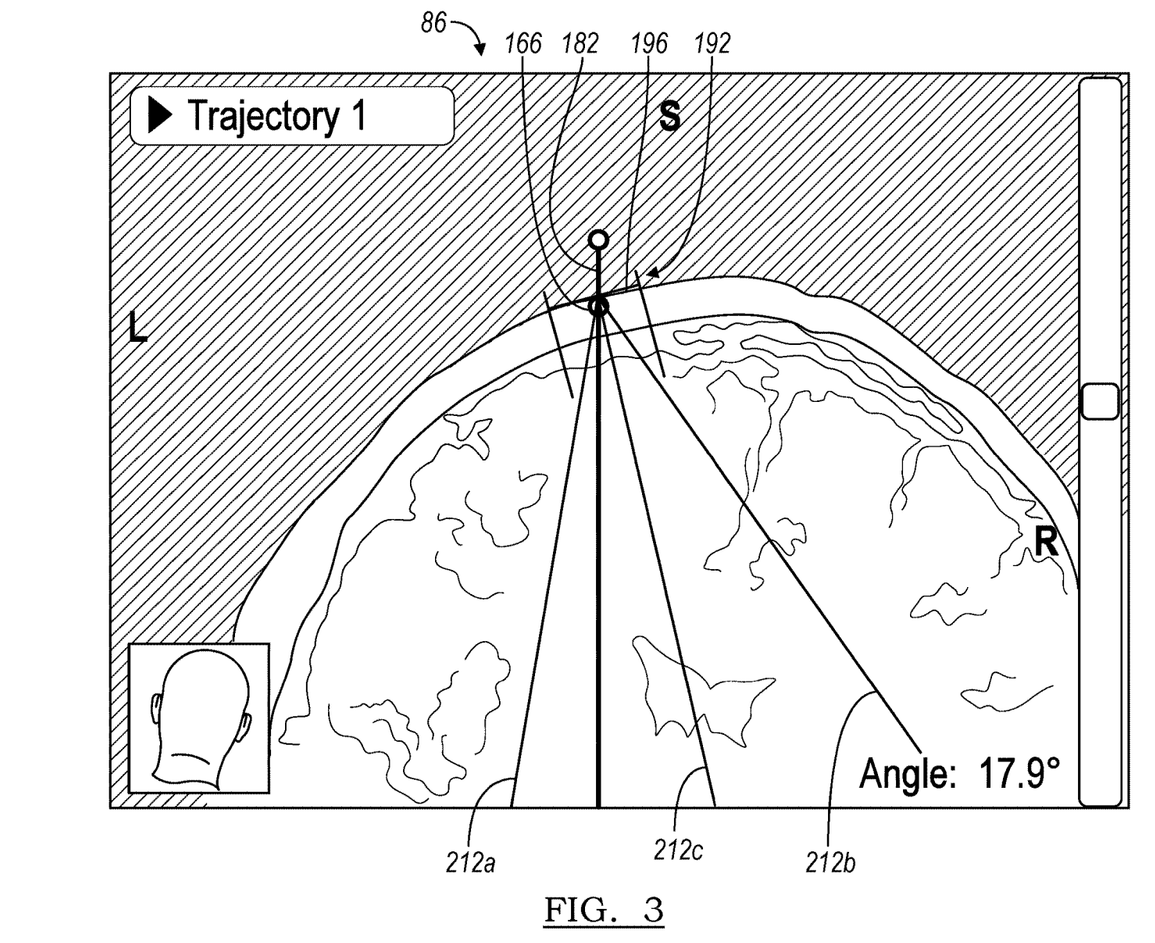
FIG. 3 is a second image based on image data acquired of a subject, according to various embodiments.
Figure 4:
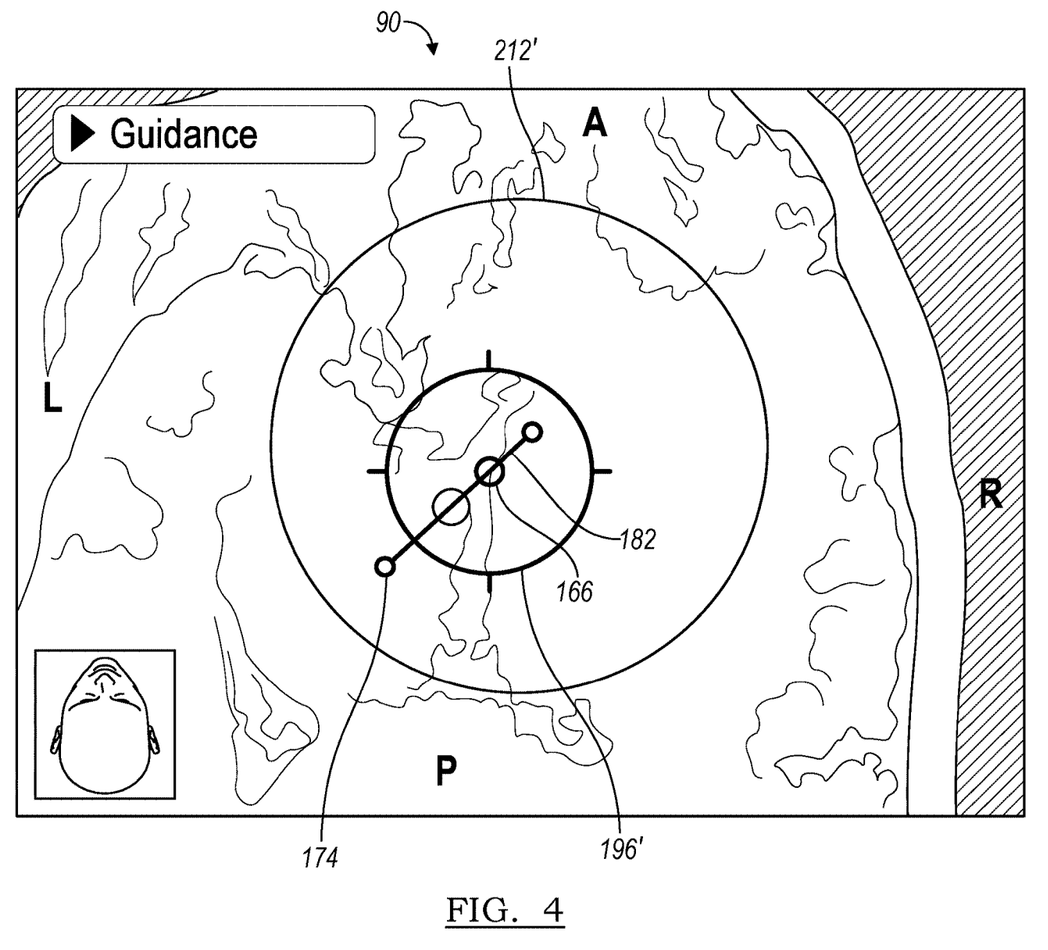
FIG. 4 is a is a first image based on image data acquired of a subject, according to various embodiments.

A first image view 80 is illustrated in FIG. 2. The image view 80 may be at a selected orientation relative to a subject 82. FIG. 3 illustrates a second image 86 at a different or alternative perspective relative to the subject 82. FIG. 4 illustrates an image 90 at a third perspective relative to the subject 82 and may also be an instrument "eye-view", such as along a long axis of the instrument. FIG. 5 illustrates a screen shot where a view may include a plurality of views of the subject.

With continuing reference to FIGS. 2-5, the user 60 may acquire image data of the subject 82 with a selected imaging system, such as the imaging system 50 illustrated in FIG. 1, or any other appropriate imaging system. Image data may be acquired with various two-dimensional imaging modalities such as a C-arm or other appropriate two-dimensional x-ray imaging system, as discussed further herein. Further, three-dimensional image data may be acquired of the subject 82 using various imaging modalities including magnetic resonance imaging (MRI), computed tomography (CT), or other imaging modalities. It is understood, however, that three-dimensional images may be reconstructed based on two or more two-dimensional images. In addition, two-dimensional images may be made based on three-dimension image data, as is understood by one skilled in the art.

The images 80, 86, 90, and 40 may be used by the user 60, as discussed further herein, to plan a procedure on the subject 82. The planning of the procedure for the subject 82 may include various steps or portions as illustrated in a process or flowchart 140, illustrated in FIG. 6. It is understood that the flowchart 140 may incorporate features or portions may be accessed and/or operated with either or both of the navigation system 34 or the planning system 100. For example, the user 60 may perform an entire planning procedure prior to entering an operating room or without the patient 82 present, but may use either the planning system 100 or the navigation system 34. Further, during a procedure, the user 60 may plan various portions of the procedure, such as selection of the guide 128 and/or placement of an access portal, and may use only the navigation system 34 or the planning system 100. Thus, it is understood that the planning process, such as illustrated within the flowchart 140 may be performed with any appropriate system.

Figure 6:
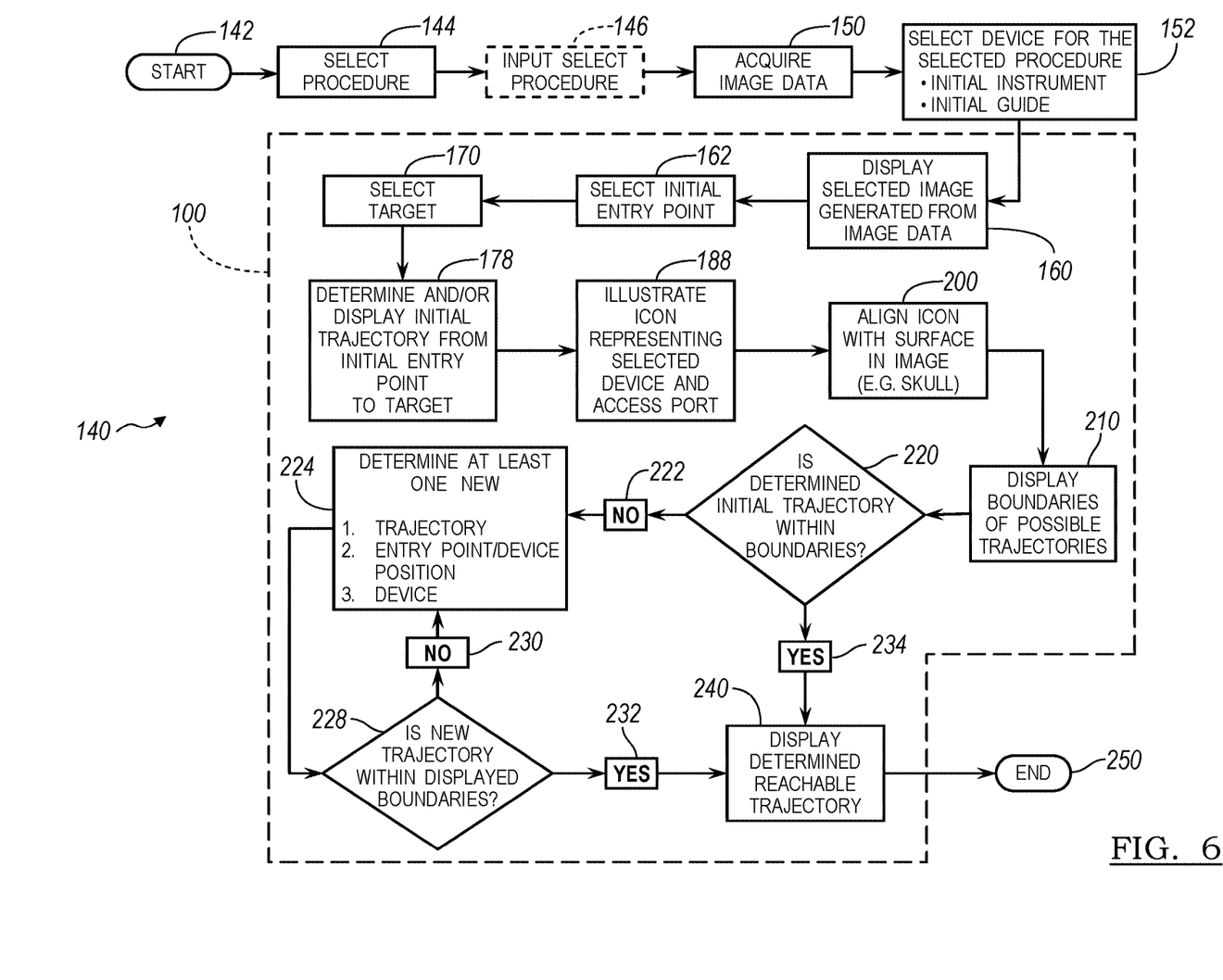
FIG. 6 is a flow chart of a illustrating a process for planning a procedure.

Further, various processes illustrated in the flowchart 140 are performed by a processor, such as one or both of the processor 106 and/or the processor 36 based upon inputs from the user 60 or other appropriate user and executing instructions stored in a selected memory. Therefore, it is understood that various features of the flowchart 140 may be formed as instructions or formulated as an algorithm that can be incorporated into instructions to perform various steps or features as discussed further herein.

The flowchart 140 may, therefore, start at a start block 142. A user, such as the user 60, may select a procedure. For example, a surgeon may select a brain tumor biopsy of the subject 82 in block 144. It is understood, however, that other appropriate procedures may also be selected such as implanting a deep brain stimulation (DBS) lead or probe, inserting or assembling a selected construct, or the like. Once a procedure is selected in block 144, however, the selected type of procedure may be input into the planning system 100 in block 146. It is understood that inputting the selected procedure in block 146 into the planning system 100 may be optional; however, the planning system may include instructions to assist in selecting types of data and selecting instrumentation for performing a procedure. The input may include the user 60 selecting from a menu a type of procedure, or selecting various instruments and guides for a procedure. It is understood, however, that the user 60 may also select various options such as the type of data to acquire, instrumentation to use, and the like.

Acquiring image data in block 150 may therefore be based upon an input from the user 60, directly alone, or based upon a determination or automatic selection by the planning system 100. The automatic selection of the type of image data may be transmitted directly from the planning system 100 to the imaging system 50 with a transmission line 56', as illustrated in FIG. 1. The user 60, however, in determining or selecting the acquisition of image data in block 150 may also transmit instructions to the imaging system 50, via the transmission line 56'. The user 60, however, may also communicate the type of image data to be acquired in any other appropriate manner, such as via oral communication, messaging, or the like to an operator of the imaging system 50. The image data of a point or portion of interest of the subject 82 may then be acquired in block 150 with the imaging system 50 for use in planning a procedure.

Selecting a device for the selected procedure may occur in block 152. The selection of the device may occur concurrently with, before, or after the acquisition of image data in block 150. The placing of the selection of the device in block 152 to follow the acquisition of the image data 150 is merely exemplary. However, the selection of the device in block 152 may be used by the planning system 100 to assist in preparing or finalizing a plan for performing a procedure on the subject 82. The subject procedure in block 144 may use one or more instruments that are positioned within the cranium 124 of the subject 82. The selection of the device 152 may include the selection of the instruments to be positioned into the patient 82. Further, the selection of the device in block 152 may include the selection of more than one device and/or devices that will be used together. For example, one or more guide devices 128 may be selected to assist in guiding the instrument 120 into the patient 82. In addition, the selection may include a guide and an instrument to be guided by the guide.

The selected device(s), which may include the instrument 120 and the guide 128 and are used to assist in determining selected geometries, dimensions, and the like for using the instrument 120. Accordingly, the selection of the device in block 152 may be used by the planning system 100, as discussed further herein, to assist in planning a procedure by determining appropriate or limitations on dimensions and movement of the instrument 120 and/or the guide 128. The selected geometries or range of motion or reachability may include various shapes that are defined by a range of motion (e.g. multiple degrees of motion). Shapes may include spheres, cones, cubes, rhombus, etc. As discussed herein, a volume of reachability may be determined and displayed, such as relative to an image, for viewing and further determination.

With continuing reference to FIG. 6 and FIGS. 2-5, the planning system 100 may be used to assist in selecting or confirming a trajectory for a procedure. The flowchart 140 illustrates that after selecting the device for a selected procedure, a process that may be executed by the planning system 100 automatically or in combination with the user 60 is may be entered. A display device, such as the display device 102, may display the selected image in block 160. Displaying the selected image may include any appropriate or any number of selected images, as illustrated in FIGS. 2-5. The displayed image may be of an entire portion of a subject, such as an entire head 124 or may include a selected portion thereof, such as a medial superior portion of the cranium 124, as illustrated in FIG. 2. The planning system 100 may then automatically or with an input may be made to select an initial entry point in block 162. For example, the user 60 may use the user input 104 to select an entry point 166, as illustrated in FIG. 2. Alternatively, the processor 106 may execute instructions to determine an initial entry point 166, such as segmenting the image to determine a flat portion or a point nearest a determined tumor, etc. The entry point 166 in the image 80 may be any appropriate size, but may be represented by a selected one or more pixel/voxels or sub-pixel/voxel portion. As discussed further herein, various other information may be illustrated and determined relative to the entry point 166.

A target may be selected in block 170 which may be illustrated with a target icon 174 on the image 80. The selected target in block 170 may be a part or all of a selected region of the subject 82, such as within a tumor for performing a biopsy. The selected target may also be based upon various anatomical or other information. For example, an atlas image may be registered to the image 80 and an anatomical, including a functional portion, of the anatomy may be selected as the target in block 170. Therefore, the selected target in block 170 may be visible to the user 60 or invisible to the user 60, but selected based upon determinations relative to whether information, such as with an atlas, visible anatomical features, or the like.

Once an initial entry point is selected in block 162 and a target is selected in block 170, a determined and/or displayed initial trajectory from the initial entry point to the target may be made in block 178. The initial trajectory may also be illustrated as a trajectory icon 182 superimposed on the image 80 with the display device 102. The trajectory icon 182 may be illustrated in any appropriate manner, such as a straight line. The processor 106 may calculate and display a straight line between and/or through the entry point 166 and the target 174 for display on the image 80. It is understood, however, that the trajectory icon 182 may be determined to be a non-straight line and may include one or more curves along the path from the entry point 166 to the target 174. The trajectory icon 182 may also be assisted or determined in part by the user 60. For example, the user 60 may determine the target 174 and draw or drag a ray or line from the target 174 to a point that may become the selected initial entry point of block 162. Nonetheless, according to various embodiments, the processor system 106 may execute instructions calculating a line between points determined as the selected initial entry point in block 162 and a selected target in block 170. The determination of the line may be made by determining or identifying at least one pixel or voxel within an image for each of the entry points 166 and the target 174 and calculate a line between the two points.

Once the selection of the initial point entry point in block 162 is made, an illustration of a device icon 192 representing the selected device and/or access port may be made in block 188. The illustration of the device icon 192 may include illustrating at least a first line 194a and second line 194b that are parallel to one another on the two-dimensional image 80. Further, a third line 196, perpendicular to both the first and second lines 194a, 194b, may be illustrated interconnecting or between the two parallel lines 194a, 194b. The icon 192 may be illustrated substantially after the determination of the initial entry point 166 and/or at any other appropriate time such as after determining the trajectory in block 178.

The device icon 192 may represent at least a portion of the selected device, such as the guide 128. The parallel lines 194a and 194b may represent the dimensions of a burr or access portal to access the interior of the cranium 124 of the subject 82. The third line 196 may illustrate the base of the guide 128 that will rest or be fixed to an outer surface 198 of the cranium 124 of the subject 82. The parallel lines 194a and 194b in combination with the third line 196 illustrate the dimensions through which the instrument 120 may or must pass along the trajectory 182. As discussed further herein, these may be used in determining whether the initial trajectory 182 is within a possibility of a boundary of motion or guiding of the guide 128. The device (e.g. a guide) may be positioned at any appropriate point on the patient 82. Therefore, the device icon 192 may be moved on the display device relative to the image 80, thus the lines representing the device icon 192 may move to illustrate the boundaries relative to the guide device icon 192 and the image 82.

After illustrating the device icon 192 in block 188, the device icon 192 may be aligned with a surface 198 of the image 80 in block 200. The processor 106 of the planning system 100 may attempt to identify a surface or position the line 196 tangent to a curve at the entry point 166. The user 60, however, may also use the user input 104 to alter or move the line 196 to position it at a point that is substantially flat or aligned on the surface 198 of the image 80. By ensuring that the line 196 is flat or in most contact with the surface 198, the true extent or possible boundaries of trajectories may be known relative to the guide 128.

The line 196, of the device icon 192, once aligned with the outer surface 198 of the image 80 may be used by the planning system 100 to identify geometries or ranges of reachability or procedural limits relative to the line 196, which represents the guide 128. As discussed above, the line 196 represents a surface of the guide 128 that will be positioned on the skull 124 of the subject 82. Therefore, the line 196 determines the selected geometry of the guide 128 and an extent of possible guiding of the instrument 120 within the subject 82. Accordingly, once the device icon 192 is aligned in block 200, a display of boundaries of guiding or an area or volume of reachability may be illustrated. The area or volume of reachability may include or define a boundary of all trajectories possible to be guided with the guide 128 and may be displayed in block 210. The user 60 may be able to determine, prior to performing a procedure, whether a planned trajectory is possible, such as able to be guided by a guide device.

A boundary line or set of boundary lines 212 may be defined relative to the line 196 of the device icon 192 and may include one or more boundary lines illustrated as icons superimposed on the image, such as a first boundary line 212a, a second boundary line 212b, and a third boundary line 212c. The boundary 212 may also include a base 212d that is illustrated. The base 212d may be a distance 213 from the line 196 and that may be measured along a line normal to the line 196. The boundaries 212 may define an entire workable or reachable volume of the selected device, such as all trajectories possible with a selected guide and/or instrument selected in block 152. In various embodiments, this may include a boundary that may be achieved by moving or adjusting the guide, such as a X or Y stage of the guide (e.g. the Nexframe® guide device and/or the guide device disclosed in U.S. Pat. Nos. 7,981,120 and 8,911,452, both incorporated herein by reference). Thus, based upon information regarding the instrument selected and device selected, boundaries 212 may be determined and/or recalled regarding angle of deflection from a center line/line normal to the line 196 and a depth from the entry point 166.

The boundary lines 212 may be defined by a cone, such as a right circular cone, having an apex or vertex at the entry point 166 and a based a distance into the subject 82 represented in the image 80. The base 212d may be a height of the cone 213 from the entry point 166. The apex of the cone defined by the boundary lines, however, may be above or below the line 196 and/or the entry point 166. The boundary lines 212 represent the cone having a selected angle relative to the height line that is perpendicular to the line 196 of the icon 192. The angle may be defined by various features such as geometry of the guide 128, the exterior dimensions of the burr hole, as defined by the parallel lines 194a, 194b, size of the instrument 120, or other specific geometries of features. As illustrate in FIG. 2, the two boundary lines 212a and 212b extend from a center of the line 196, such as defined by the entry point 166, out or toward the interior of the image 80. The boundary lines 212 do not contact ends of the parallel lines 194a and 194b. Therefore, the extent of the boundaries 212a-212c may be defined by the guide 128 and/or the burr hole formed through the skull 214 of the subject 82.

Although illustrated as a cone in the FIGS. 2-5, it is understood that the reachable space may be represented and/or determined to be any appropriate shape, geometry, and size. The area or volume of reachability, therefore, may be defined as any appropriate shape, and a cone or triangle is merely exemplary. For example, selected guides may be movable in straight lines on a X and Y stage, thus a volume or area of reachability may be a square or cube. Other guides may allow for more complex movements of an instrument, and the boundaries that illustrate the area of volume of reachability may be other appropriate shapes. Further, the reachability may generally be a volume. The volume may be displayed in a three-dimensional (3D) image (e.g. FIG. 5) or represented by several lines on a two-dimensional (2D) image (e.g. FIG. 2). It is understood, however, that the boundaries may be limited to an area and may be illustrated as such on relative images.

The boundary line 212 may be viewed by the user 60 and/or analyzed by the planning system 100 to determine whether the initial trajectory is within the boundary lines 212. Therefore, the flowchart 140 and the planning process 100 may include a query of determining whether the initial trajectory is within the boundaries 212 in block 220. As discussed above, the boundary 212 defines and illustrates all trajectories that are possible with the selected device (e.g. guide) at a selected location and position of the device.

If the initial trajectory is not within the boundaries 212, a no path 222 may be followed to determine alter or select a new trajectory, new entry point, and/or new device in block 224. Selected feedback may be provided to the user 60, such as a display, sound, tactile, or other feedback to indicate that the initial trajectory 182 is not within the boundaries 212. Thus, the initial trajectory is not within the cone of reachability of the guide 128 that is represented by the icon 192. The feedback may be provided to the user 60, directly, and/or as an instruction to the planning system 100 to alter a parameter to generate a new trajectory, as discussed herein, including selecting a new entry point, moving a guide relative to the selected entry point, etc.

The trajectory 182, as discussed above and illustrated in FIG. 2, may be an initial trajectory from the selected initial entry point 166. The target 174 may be within an area that may include possible alternative target locations, such as within a tumor. Therefore, the target may be altered relative to the initial entry 166 and a new trajectory 182' may be determined. In addition, or alternative to altering the location of the target 174 to calculate the new trajectory 182' a new or alternative entry point 166', different from the initial entry point 166, may be made. Changing the initial entry 166 to the alternative entry point 166' may form the alternative or new trajectory 182' to even the same target 174. Also, the device icon may be changed to represent a new or different device (such as a straight or an angled guide). Further, the icon 192 may be moved to represent moving the guide relative to the selected initial entry point 166, which, in turn, moves the boundaries 212 as well. Thus, multiple changes may be made to determine a new trajectory in block 224.

On the display 102, the device icon 192 in combination the boundary lines 212 may then be moved relative to the new entry point 166' and illustrated relative to the new trajectory 182'. Accordingly, the trajectory may be altered by selecting a target different than the initial target 174 and maintaining the initial entry point 166, selecting the new entry point 166' while maintaining a target, or altering the shape of the trajectory 182. Regardless, if the initial trajectory 182 is not within the boundary lines 212 the new trajectory 182' may be determined by block 224. A further query block may then be used to determine if the new trajectory 182' is within the displayed boundaries in block 228.

If the new trajectory 182' is not within the boundaries 212, a no path 230 may be followed to determine a new trajectory and/or new entry point in block 224. The same alterations, as discussed above, may be made to determine a new trajectory and query whether the new trajectory is displayed within the boundaries of block 228 may again be determined. Accordingly, an iterative process may be entered to determine a trajectory that is within the boundaries 212 by varying the parameters, as discussed above, such as the entry point, target point, trajectory shape, guide, etc.

After a new trajectory is determined in block 224 and the query of whether the new trajectory is within the displayed boundaries 212 in block 228, is positive or yes determination is made, a yes path 232 may be followed. Similarly, if the initial trajectory 182 is determined to be within the boundaries 212 in block 220 a yes path 234 may also be followed.

Both yes paths 232, 234 may follow to display a reachable trajectory in block 240. A reachable trajectory is a trajectory that is within the boundary lines 212 and may be displayed on the display device 102 of the planning system 100. It is understood that a reachable trajectory may be substantially within the boundary lines 212. For example, an error or tolerance of about 0.01 millimeters (mm) to about 3 mm may be used. Thus, even if the trajectory is touching or extends past the boundary line by about 3 mm it may be determined to be a reachable trajectory.

Once the determination is made of a reachable trajectory, as discussed above, the reachable trajectory may be saved as a plan (i.e. a predetermined plan) by the planning system 100 and/or the user 60 in the memory 108 for a selected procedure. The planning system 100 may then be used as the navigation processor system 34 and/or the plan may be transferred to navigation processor system 34 for performing a guided procedure. Alternatively, or in addition thereto, it is understood that a guided procedure is not required to occur, but rather that the planning system 100 may be used to plan a portion of the procedure that may occur without a navigation system.

The planning system 100 may be used to determine and plan the entry point 166 and the location of the guide 128 to ensure that the trajectory 182 is within the boundaries 212 to reach the target 174. A navigation system may not be required to ensure that the instrument 120 reaches the target 174 once the reachable trajectory is determined based on the entry point 166 relative to the geometry of the guide and reachability as defined by the boundary lines 212. For example, the guide 128 may be positioned on the subject 82 based upon the planned position of the device icon 192. The trajectory 182, including path and distance, for moving the instrument 120 into the subject 82 may be measured without a tracking system, as is understood by one skilled in the art. For example, a guide portion may be set at a selected angle and a length of the instrument 120 may be preset with a stop. Accordingly, the process 140 may end in block 250.

It is understood that the end block 250 is the end of the planning process and may be the beginning the procedure on the subject 82. The plan including the position of the guide 128 based upon the position of the device icon 192 and the determined reachable trajectory 182 to reach the target 174 may be the results and the output of the process 140. The planning system 100 may display the icons, as discussed above, on the image 80, as illustrated herein and discussed above, including positions for forming the burr hole into the subject 82, a position for the guide 128, and a trajectory 182 of the instrument 120. Therefore, the planning system 100 may output for viewing by the user 60 a selected display including a display on the display device 102 and/or the display device of 42. The display may include the image 80 including the icon 192 and the trajectory 182 superimposed thereon. Any additional or further forms of output may include specific location and instructions, the length of the instrument 120, and other physical outputs to be used by the user 60.

Further, it is understood that the image may be displayed with an icon of any appropriate type. For example, with reference to FIG. 3, the icon 192 may be displayed on a substantially posterior two-dimensional image 86 of the subject. With further reference to FIG. 4, it is understood that the boundary lines 212 may be illustrated as a circle 212' and the line 196 may be illustrated as a circle 196'. As discussed above, the boundaries 212 may represent a cone or an exterior of a cone and the circle 212' may illustrate the base of the cone or a perimeter of a cross-section of the cone at the depth of the target 174. The circle 196' may illustrate the line 196 which represents the guide 128. Again, the trajectory 186 may be illustrated as well from the entry point 166 to the target 174. Further, with reference to FIG. 5, a three dimensional rendering image 260 may have a boundary 212" illustrated as a three dimensional cone relative to the three dimensional rendering image 260. The trajectory 186 may also be illustrated relative to the three dimensional cone boundary 212" illustrated relative to the superimposed on the three dimensional rendering 260. Accordingly, it is understood that the boundaries and/or the trajectory 186 may be illustrated in the various matters relative to different perspectives and different dimensionalities of the image.

According to various embodiments, a navigated procedure may be selected. The plan saved in the memory 108 may be used with the navigation system 36 to navigate and guide the instrument 124 into the subject. As discussed herein, the instrument 124 may be tracked and may the position of the guide 128. The position of the instrument 124 may be illustrated as an instrument icon relative to the reachable trajectory or plan icon on the display device 42.

Thus, returning reference to FIG. 1, the suite 20 is illustrated that includes navigation system 22 that can be used for various procedures. The navigation system 22 can be used to track the location of an item, such as an implant or the instrument 124, relative to the subject 82. It should further be noted that the navigation system 22 may be used to navigate any type of instrument, implant, or delivery system, including: guide wires, arthroscopic systems, orthopedic implants, spinal implants, DBS leads, cardiac pacing leads, ablation instruments, etc. Moreover, the instruments may be used to navigate or map any region of the body. The navigation system 10 and the various tracked items may be used in any appropriate procedure, such as one that is generally minimally invasive or an open procedure.

The navigation system 22 can interface with the imaging system 50 that is used to acquire pre-operative, intra-operative, or post-operative, or real-time image data of the patient 82. It will be understood by one skilled in the art, any appropriate subject can be imaged and any appropriate procedure may be performed relative to the subject. The subject may be a human patient and the procedure may be a surgical procedure, such as an implantation of a device (e.g. a screw, lead, etc.).

Exemplarily illustrated in FIG. 1, the imaging system 50 comprises an O-arm® imaging device sold by Medtronic Navigation, Inc. having a place of business in Louisville, Colorado, USA. The imaging device 50 may have a generally annular gantry housing 270 that encloses an image capturing portion 272. The image capturing portion 272 may include an x-ray source or emission portion 274 and an x-ray receiving or image receiving portion 276 located generally or as practically possible 180 degrees from each other within the gantry housing 270. In various embodiments, the x-ray source or emission portion 274 and the x-ray receiving or image receiving portion 276 may be mounted on a rotor (not illustrated) relative to a track (not illustrated) within the generally annular gantry housing 270. The image capturing portion 272 can be operable to rotate 360 degrees during image acquisition. The image capturing portion 272 may rotate around a central point or axis, allowing image data of the patient 82 to be acquired from multiple directions or in multiple planes. The imaging system 50 can include those disclosed in U.S. Pat. Nos. 7,188,998; 7,108,421; 7,106,825; 7,001,045; and 6,940,941; all of which are incorporated herein by reference. The imaging system 50, however, may also include or be replaced with other imaging systems including C-arm fluoroscopic imaging systems, computer tomography (CT) imaging systems, etc. which can also generate three-dimensional views of the patient 82.

The position of the image capturing portion 272 can be precisely known relative to any other portion of the imaging device 50. In addition, as discussed herein, the precise knowledge of the position of the image capturing portion 272 can be used in conjunction with the tracking system to determine the position of the image capturing portion 272 and the image data relative to the subject, such as the patient 82, which is tracked. For example a patient tracking device 280 may be placed on the patient 82 to track the patient 82.

The tracking system 24 can include various portions that are associated or included with the navigation system 22. The tracking system 24 can also include a plurality of types of tracking systems including an optical tracking system that includes an optical localizer 26 and/or an electromagnetic (EM) tracking system that can include an EM localizer 28. The optical localizer 26 may "view" or optically track trackable portions (tracking devices) with cameras. The EM localizer 28 may generate a field and a trackable portion (e.g. EM tracking device) may sense the field to determination a location relative to another tracking device in the field. Various tracking devices, including those discussed further herein, can be tracked with the tracking system 24 and the information can be used by the navigation system 22 to allow for a display of a position of an item. Briefly, tracking devices, such as a patient tracking device 280, an imaging device tracking device 282, and an instrument tracking device 284, allow selected portions of an operating theater to be tracked relative to one another with the appropriate tracking system 24, including the optical localizer 26 and/or the EM localizer 28.

It will be understood that any of the tracking devices 280, 282, 284 can be optical or EM tracking devices, or both, depending upon the tracking localizer used to track the respective tracking devices. It will be further understood that any appropriate tracking system can be used with the navigation system 22. Alterative tracking systems can include radar tracking systems, acoustic tracking systems, ultrasound tracking systems, and the like.

An exemplarily EM tracking system can include the STEALTHSTATION® AXIEM™, STEALTHSTATION® S7™, or STEALTHSTATION® i7™ Navigation Systems, sold by Medtronic Navigation, Inc. having a place of business in Louisville, Colorado. Exemplary tracking systems are also disclosed in U.S. Pat. No. 8,644,907, issued Feb. 4, 23012, titled "Method And Apparatus For Surgical Navigation"; U.S. Pat. No. 7,751,865, titled "Method And Apparatus For Surgical Navigation", issued Jul. 6, 2010; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated by reference herein.

Further, for EM tracking systems it may be necessary to provide shielding or distortion compensation systems to shield or compensate for distortions in the EM field generated by the EM localizer 28. Exemplary shielding systems include those in U.S. Pat. No. 7,797,032, titled "Method and system for navigating a catheter probe in the presence of field-influencing objects", issued on Sep. 14, 2010 and U.S. Pat. No. 6,747,539, titled "Patient-shielding and coil system", issued on Jun. 8, 2004, all of which are incorporated herein by reference. Distortion compensation systems can include those disclosed in U.S. Pat. No. 6,636,757, titled "Method and apparatus for electromagnetic navigation of a surgical probe near a metal object", issued on Oct. 21, 2003, all of which are incorporated herein by reference.

With an EM tracking system, the EM localizer 28 and the various tracking devices can communicate through an EM controller within the CAC/NII 30. The EM controller can include various amplifiers, filters, electrical isolation, and other systems. The EM controller can also control the coils of the localizer 28 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller.

It will be understood that the tracking system may also be or include any appropriate tracking system, including a STEALTHSTATION® TRIM®, TREON®, and/or S7™ Navigation System having an optical localizer, similar to the optical localizer 26, sold by Medtronic Navigation, Inc. having a place of business in Louisville, Colorado. Optical tracking systems may also include those discloses in U.S. Pat. No. 8,010,177, Aug. 30, 2011, Intraoperative Image Registration"; U.S. Pat. No. 6,235,038, issued on May 22, 2001, titled "System For Translation Of Electromagnetic And Optical Localization Systems", all incorporated herein by reference. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 50 can include the support housing or cart 54. The imaging system 50 can further include the separate image processing unit 52 that can be housed in the cart 54. The navigation system 22 can include the navigation processing unit 36 that can communicate or include a navigation memory 38. The navigation memory 38 may include any appropriate non-transitory memory including a random access memory, magnetic media drive, etc. Further, the navigation memory 38 may be integrated with the navigation processing unit 36 or remote from the navigation processing unit 36. The navigation processing unit 36 can receive information, including image data, from the imaging system 50, plan information from the planning system 100 (if planned separately from the navigation system 34), and tracking information from the tracking systems 24, including the respective tracking information from the tracking devices 280, 282, 284 and the localizers 26, 28. Image data can be displayed as the image 40 on the display device 42 of the workstation or other computer system 34. The workstation 34 can include appropriate input devices, such as user input devices including a keyboard 290. It will be understood that other appropriate input devices can be included, such as a mouse, a foot pedal or the like. The various processing units and computers or workstations may include internal or local memory and processing units. The processing units may include central processing units that are general computers that execute instructions to perform tasks on a chip. The processing units may also be specific circuits, such as application specific integrated circuits (ASIC). Accordingly, the processing units may be devices that receive information and execute instructions that are stored or received based on the information.

The image processing unit 52 may process image data from the imaging system 50 and transmits it to the navigation processing unit 36. It will be further understood, however, that the imaging system 50 need not perform any image processing and it can transmit the image data directly to the navigation processing unit 36. Accordingly, the navigation system 22 may include or operate with a single or multiple processing centers or units that can access single or multiple memory systems based upon system design.

The patient 82 can be fixed onto an operating table 292, but is not required to be fixed to the table 292. The table 292 can include a plurality of straps 72944. The straps 294 can be secured around the patient 82 to fix the patient 82 relative to the table 292. Various apparatuses may be used to position the patient 82 in a static position on the operating table 292. Examples of such patient positioning devices are set forth in commonly assigned U.S. patent application Ser. No. 10/405,068, published as U.S. Pat. App. Pub. No. 2004/0199072, entitled "An Integrated Electromagnetic Navigation And Patient Positioning Device", filed Apr. 1, 2003, which is hereby incorporated by reference. Other known apparatuses may include a Mayfield® clamp.

Also, the position (including three-dimensional location and orientation) of the patient 82 relative to the imaging system 50 can be determined by the navigation system 22 with the patient tracking device 280 and the imaging system tracking device 282. As discussed herein, the position (including three-dimensional location and orientation) relative to the patient 82 may be determined, at least in part, with images acquired of the patient 82. Accordingly, the position (including three-dimensional location and orientation) of the patient 82 relative to the imaging system 50 can be determined. The imaging system 50, such as the O-arm® can know its position and be repositioned to the same position within about 10 microns. This allows for a substantially precise placement of the imaging system 50 and precise determination of the position of the imaging device 50. Precise positioning of the imaging portion 272 is further described in U.S. Pat. Nos. 7,188,998; 7,108,421; 7,106,825; 7,001,045; and 6,940,941; all of which are incorporated herein by reference. Generally, it may be selected to determine the position of the image data relative to the patient 82. For example, the position, including the orientation relative to the patient, of the image data may be used to determine a location of a portion of the patient 82.

Subject or patient space and image space can be registered by identifying matching points or fiducial points in the patient space and related or identical points in the image space. The imaging device 50, such as the O-arm® imaging device sold by Medtronic, Inc., can be used to generate image data at a precise and known position. This can allow image data that is automatically or "inherently registered" to the patient 82 upon acquisition of the image data. Essentially, the position of the patient 82 is known precisely relative to the imaging system 50 due to the accurate positioning of the imaging system 50 relative to the patient 82. This allows points in the image data to be known relative to points of the patient 82 because of the known precise location of the imaging system 82.

Alternatively, manual or automatic registration can occur by matching fiducial points in image data with fiducial points on the patient 82. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, now published U.S. Pat. App. Pub. No. 2010/0228117, incorporated herein by reference.

Once registered, the navigation system 22 with or without the imaging system 50, can be used to perform selected procedures. Accordingly, it is understood that the subject 82 need not be within the imaging system 50 during a navigated procedure. The subject 82 may be away from the imaging system 50 but the instrument 120 may be tracked.

Selected procedures can use the image data generated or acquired with the imaging system 50. Further, the imaging system 50 can be used to acquire image data at different times relative to a procedure. As discussed herein, image data can be acquired of the patient 82 subsequent to a selected portion of a procedure for various purposes, including confirmation of the portion of the procedure.

With continuing reference to FIG. 1, the imaging system 50 can generate actual or virtual three dimensional images of the patient 82. The patient 82 can be placed relative to the imaging system 50 to allow the imaging system 50 to obtain image data of the patient 82. To generate 3D image data, the image data can be acquired from a plurality of views or positions relative to the patient 82. The 3D image data of the patient 82 can be used alone or with other information to assist in performing a procedure on the patient 82 or an appropriate subject. It will be understood, however, that any appropriate imaging system can be used, including magnetic resonance imaging, computed tomography, fluoroscopy, etc. to acquire image data (including 3D image data) of the patient 82.

As discussed above, the user 60 may use the plan to perform the procedure. With reference to the figures, including FIG. 1 and FIG. 5, the instrument 120 may be tracked. The tracking device 284 coupled to the instrument 120 may include any appropriate tracking device, such as a reflector array viewable by the optical localizer 26 or an EM coil operable with the EM localizer 28. Nevertheless, the position of a portion (such as a distal tip) of the instrument 120 may be tracked. The tracked position may be illustrated as an instrument icon 300 superimposed on the image 40 with the display device 42. the user 60 may view the display device 42 and see the tracked position of the instrument by viewing the instrument icon 300. The position of the instrument 120 relative to the preplanned reachable trajectory 182 may also be viewed.

Initially, the formation of an entry portal at the entry point 166 may be tracked by tracking the instrument to form the entry portal at the entry point may be tracked. As noted above, the entry portal may include any appropriate portal, including selected craniotomies such as burr holes. The tracked position of the portal forming instrument may be displayed with the display device 42. Also, the position of the guide 128 maybe tracked as it is positioned on the cranium 124. Also, the angle or position of the guide relative to the patient 82 may be tracked.

In addition to or alternatively to, pre-planning the position of the device with the planning system 100, the panning system 100 and/or the navigation system 32 may be used to determine, during a procedure, a position for at least one of the device (e.g. guide 128) or the entry point. For example, the guide 128 may be tracked with a guide tracking device 310 (e.g. similar to the tracking devices discussed above) and the position of the guide may be tracked with the tracking systems 24. Thus, the device icon 192 and the boundaries 212 may be displayed on the display device 42, such as superimposed on the image 40. The user 60 may move the guide 128 and the device icon 192 and the boundary lines 212 may be moved on the display device 42 based on the tracked position of the guide 128. In this way, the guide 128 may be selectively positioned during a procedure to ensure that the volume or area of reachability of the guide 128 will include the planned trajectory 182. The trajectory 182 may be planned at any appropriate time as well, such as prior to or during the procedure. The trajectory 182 may be displayed with the display device 42 relative to the boundary lines 212.

When the guide 128 is tracked, the user 60 may view the display 42 to determine that the boundaries 212 of the area or volume of reachability of the guide 128, or other appropriate device, overlaps or includes the planned trajectory 182 when positioned near and/or on the patient 82, but prior to fixation to the subject 82. The boundaries 212 may include dimensions input by the user 60 and/or selected from a menu. The user 60 may select the guide 128 from a menu and the processor 36 and/or 106 may recall the dimensions and geometry of the boundaries 212 from the memory 38 and/or 108. Nevertheless, the device icon 192 and the boundaries 212 may be displayed on the display device 42 based on the tracked position of the guide 128 relative to the subject 82 with the tracking system 24. This may also allow the user 60 to alter (e.g. move within a burr hole) the position of the guide 128 from a pre-planned position, but still determine and confirm that the planned trajectory 182 is within the area or volume of reachability by viewing the display device 42 and the device icon 192 and/or the boundary 212.

As illustrated in FIG. 5, the position of the reachable trajectory is known by the preplanned position of the entry point 166 and the guide 128 determined by the line 196 and/or based on the tracked position of the guide 128. Thus, the instrument icon 300 representing the tracked position of the instrument 120 may be displayed relative to the other preplanned icons. In this way, the user 60 may determine and/or confirm that the instrument 120 is on the preplanned reachable trajectory 182. The user 60 may also know when the instrument 120 reaches the target 174 by viewing the instrument icon 300 relative to the target icon 174.

If the instrument 120 is tracked off of the preplanned trajectory, however, feedback may be provided to the user 60. For example, a visual, auditory, tactile, or other indication may be provided to the user 60 that the instrument is not tracked on the preplanned trajectory 182. Thus, the plan may be used with a navigated procedure.

Figure 7:
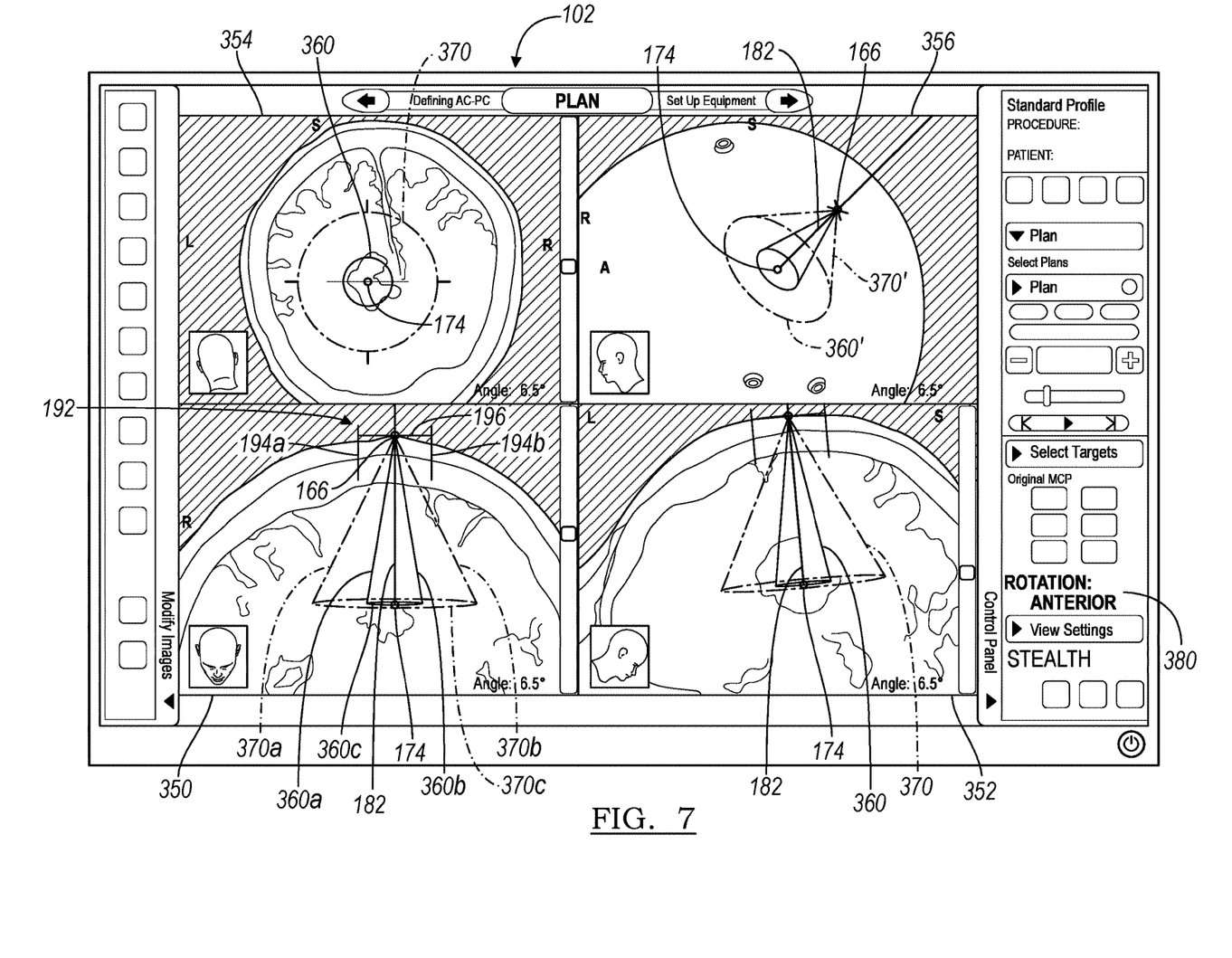
FIG. 7 is a screen shot of a display device illustrating various images and information regarding a plan for a procedure on the subject.

With continuing reference to FIG. 6 and additional of FIG. 7, the flowchart of 140 may be used for selecting or confirming an appropriate device, such as the guide 128. As discussed above, various guides may have selected the limitations, and/or features. For example, a guide may include a guide system that has two guide bodies, one with a straight guide portion and/or one with an angle guide portion, such as the straight or angled Navigus® guide system sold by Medtronic Navigation, Inc. In a two part guide system, a straight guide may include a guide tube that is substantially perpendicular to a base affixed to the cranium 124. An angled guide, however, may include a tube angled relative to a base that is fixed to the cranium 124. Therefore, different boundaries of an area or volume of reachability may be provided or defined by the two different guide portions. Accordingly, with reference to FIG. 7, an image 350, 352, 354, and 356 may be displayed on a display device, such as the display device 102.

As illustrated in the flowchart 140 an initial selection of a device, including a guide, may be in block 152. A display of boundaries for the selected device may be displayed in block 210, as illustrated in FIG. 7. The boundaries illustrated, however, may include a plurality of boundaries or ranges based upon a selected set of guides. Thus, a set of boundaries may be illustrated with one or more boundary icons representing different boundaries of possible trajectories. In various embodiments, as discussed above, a guide system may include two guides, such as one with an angled tube relative to a base and one with a more straight tube a relative base. The straight to guide may include a narrow or smaller boundary 316, which may be a cone shaped volume including a first boundary line 360a, a second boundary line 360b extending to a base 360c. The boundary 360 may be illustrated relative to the trajectory 182. With reference to the image 350 in FIG. 7, the trajectory 182 is within the boundary 360. Further, the boundary 360 may be similar to the cone shaped boundary, as discussed above, including a height that defines a workable and reachable volume by a selected instrument and/or guide combination. The boundary may illustrate any appropriate or selected shape boundary, also as discussed above.

It is understood, however, that the trajectory 182 may not be within the boundary 360. The alternative or second boundary 370 may include a second boundary icon an illustration of a first boundary line 370a, a second boundary line 370b, and a base 370c. The second or outer boundary 370 may be a shape similar to the inner or smaller boundary 360 or may be an alternative shape. As illustrated in FIG. 7, the outer boundary 370 is also a cone shape and has an apex at the same position as the inner or smaller boundary 360, generally at the entry 166 point. The user 60 may view the display device 102 to understand and determine whether the trajectory 182 is within either or both of the boundaries 360, 370. The boundaries 360, 370 may be defined by or define a volume or area that is reachable by the instrument 124 that is selected in block 152 and/or 224. Further, the boundary 370 may be similar to the cone shaped boundary, as discussed above, including a height that defines a workable and reachable volume by a selected instrument and/or guide combination. The boundary may illustrate any appropriate or selected shape boundary, also as discussed above.

The user 60 may determine which of the two trajectory portions (e.g. straight or angled) is necessary or selected to include an area or volume of reachability that includes the trajectory 182. Accordingly, rather than altering or selecting a different entry point of trajectory, the user 60 may select an appropriate guide device to achieve the selected trajectory 182. Further, the boundaries 360 and 370 illustrate a workable or reachable volume in addition to angle of deflection boundaries relative to a line normal to the line 196 and the entry point 166.

In addition, the boundary 370 may illustrate all possible or an expanse of possible boundaries of the guide device depending upon a selected position of the guide 128 and/or movement of the guide 128. As discussed above, the outer or larger boundary 370 may be based upon an angle guide. Therefore, being able to reach a selected portion of the outer boundary 370 may require a selected rotation or positioning of the angle guide relative to the subject 82. In other words, to reach the target 174, even if within all possible boundaries 370, may require a specific positioning of the guide 128 relative to the subject 82. Accordingly, as discussed above, the guide 128 may include the tracking device 310 or may have a trackable instrument (e.g. a probe) that is positionable in a portion of the guide (such as an angled guide tube) when positioning the guide on the cranium 124. The boundary 370 may be illustrated on the display device 102 and/or the display device 42 based upon a tracked position of the guide 128 to insure that the guide 128 is positioned that the boundary 370 encompasses the determined trajectory 182.

A rotational position may also be determined and illustrated in the planning screen such as the rotational demarcation 380. For example, an indication of Rotation: Anterior may provide an indication that the angle guide must be angled towards the anterior of the subject 82 to allow for the boundary 370 to encompass or include the determined trajectory 182. Other indications may be made or determined and displayed for the user 60 to allow for a determination and confirmation that the trajectory 182 is within the boundary 370.

With continuing reference to FIG. 7, the display device 102 and/or represented by display device 34 may also include various different views and images that include illustration of the boundaries. For example, the image 353 may also illustrate the boundary 370 and 360 relative to the trajectory 182 and the target 174. The image 352 may be rotated 90 degrees relative to the image 350 or any other rotational relative to the image 350. Further, an instrument may show the boundary 360 and 370 at a plane of the target 174 to allow the user 60 to view the trajectory along the path of the instrument 126 relative to the boundaries 360 and 370. Further, an image 356 may include a three dimensional display including a three dimensional boundary display 370' and a three dimensional boundary display 360'. Both three-dimensional boundaries 360', 370' may be illustrated relative to the determined trajectory 182, at a plane of the target 174, and the entry 116.

Accordingly, it is understood that the boundary may be illustrated on various images that are acquired in block 150. The displayed boundaries in block 210 may include the boundaries as illustrated in FIGS. 2-5 and/or as illustrated in FIG. 7. The boundaries may include a single boundary for a selected guide device or may include a plurality of boundaries for a set of guides or more than one guide. The user 60 may then determine whether the trajectory 182 is within the boundaries displayed in block 210 or alter or change at least one of the trajectory, entry point, and/or device position and/or device in block 234. Therefore, the flowchart 140 allows for determining, confirming, and/or selecting entry points, trajectories, and targets so that the instrument 126 may be guided on the determined trajectory 182 to the target 174.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of planning a procedure, comprising:
   displaying an image of a subject;
   superimposing a trajectory icon including at least a line representing a planned trajectory from a selected entry point to a selected target on the image;
   superimposing a first and second device icon representing a first and second device at the selected entry point on the image after superimposing the trajectory icon on the image; and
   superimposing simultaneously both a selected first boundary icon relating to the first device and a second boundary icon relating to the second device extending from the superimposed device icon on the image after the device icon and the trajectory icon are both superimposed on the image, wherein the first boundary icon is configured to illustrate first boundaries of reachability and the second boundary icon is configured to illustrate second boundaries of reachability;

tracking a position of the device such that the position of the device icon and the selected first boundary icon and the second boundary icon change relative to the displayed image when the device is moved;

providing feedback to a user that the trajectory icon is outside of the selected first boundary icon or the second boundary icon;

wherein the trajectory icon is viewable relative to and with the superimposed first boundary icon and the second boundary icon to represent whether the planned trajectory is reachable with an intervention device that is separate from and operable to be delivered through the device along an intervention device trajectory that is represented by the trajectory icon.

2. The method of claim 1, further comprising:

moving at least one of the first and second device icon so that a line at least one of the first and second device icon is substantially aligned on an exterior surface in the image.

3. The method of claim 2, wherein the first and second device icon is superimposed including the line and a pair of parallel lines;

wherein the pair of parallel lines are both perpendicular to the line.

4. The method of claim 1, further comprising:

selecting an alternative device;

superimposing an alternative device icon on the image, different than the first and second device icon, that represents the selected alternative device; and superimposing an alternative boundary icon different from the other first boundary icon or second boundary icon.

5. The method of claim 1, further comprising:

determining a new entry point different from the initial entry point if the trajectory icon intersects the first or the second boundary icon; and superimposing a new trajectory icon from the determined new entry point.

6. The method of claim 5, further comprising:

determining a new target if the trajectory icon intersects the first or the second boundary icon; and superimposing a new trajectory icon from the determined new entry point.

7. A system for planning a procedure, comprising:

a memory system configured to store a device icon, wherein the device icon represents a device and is configured to illustrate boundaries of reachability with an intervention device separate from and when passed through the device;

a processor system configured to execute instructions to:
access image data,
instruct a display device to display an image based on the image data,
receive input from a user input device to instruct the display device to display a trajectory icon, configured to represent a trajectory of the intervention device through the device as a line from an entry point to a target point superimposed on the displayed image, and
receive input from the user input device to instruct the display device to superimpose the device icon and a passage icon superimposed on the displayed image at a selected initial entry point after displaying the trajectory icon superimposed on the displayed image, wherein the memory system configured to store the device icon includes a first device icon and a second device icon, wherein the first device icon is configured to illustrate first boundaries of reachability of a first device and the second device icon is configured to illustrate second boundaries of reachability of a second device, wherein the display device is configured to display the device icon as at least one of a two-dimension icon or a three-dimension icon and wherein the device icon extends from the selected initial entry point toward the target point to simultaneously illustrate the first and second boundaries of reachability;

track a position of the intervention device such that the position of the trajectory icon and the device icon with the illustrated first and second boundaries of reachability change relative to the displayed image when the intervention device is moved;

provide a feedback to a user when the trajectory icon is outside of the device icon based on the tracked position of the intervention device;

wherein a user is able to view the display device to view the trajectory icon relative to a selected one of the first device icon and the second device icon and the passage icon to determine whether the trajectory is reachable with the intervention device through the device.

8. The system of claim 7, wherein the user input device is configured to be engaged by the user to move the device icon so that a line of the device icon is substantially adjacent an exterior surface in the image.

9. The system of claim 8, wherein the device icon includes the line and a pair of parallel lines;

wherein the pair of parallel lines are spaced apart and both perpendicular to the line.

10. The system of claim 7, further comprising:

wherein the user input device is configured to allow the user to select an alternative device.

11. The system of claim 7, further comprising:

wherein the processor system is configured to receive input from the user input device to select a new entry point different from the initial entry point if the trajectory icon intersects a boundary of the boundaries of reachability of the device;

wherein the processor system is configured to illustrate the device icon to illustrate boundaries of reachability with the intervention device separate from and when passed through the device at the new entry point.

12. A method of at least one of planning or confirming at least a portion of a planned procedure on a subject with image data acquired with an imaging device, comprising:

accessing the image data of the subject, wherein the image data is acquired with the imaging device;

simultaneously displaying superimposed on an image of the subject generated with the image data:

(i) a selected trajectory icon representing a planned trajectory including a line from a determined planned entry point into the subject to a target within the subject for an intervention instrument;

(ii) a set of boundary icons, wherein the set of boundary icons includes a first boundary icon representing a first boundary of possible trajectories achievable with the intervention instrument with a first guide member at the determined planned entry point and a second boundary icon representing a second boundary of possible trajectories achievable with the intervention instrument with a second guide member at the determined planned entry point;

(iii) a device icon representing a device at the determined planned entry point on the image;
tracking a position of the device such that the position of the device icon and the set of boundary icons change relative to the displayed image based on the tracked position of the device;
in response to determining the planned trajectory is not within the first or second boundaries, providing visual feedback to indicate that the trajectory is not within the boundaries; and
wherein the displayed superimposed selected trajectory icon relative to the superimposed set of boundary icons is operable to be viewed and to determine whether the selected planned entry point or the first or second guide member are possible to achieve the planned trajectory;
wherein both the first boundary icon and the second boundary icon extend from the planned entry point toward the target.

13. The method of claim 12, wherein the set of boundary icons includes a third boundary of possible trajectories achievable with a third guide member on the image at the planned entry point.

14. The method of claim 12, wherein the first boundary icon is within the second boundary icon.

15. The method of claim 12, further comprising:
evaluating whether the selected trajectory icon is within the first boundary icon;
if the selected trajectory icon is not within the first boundary icon, then displaying the second boundary icon.

16. The method of claim 1, further comprising:
wherein displaying the image includes at least displaying a first image and a second image, wherein the first image is at a different perspective relative to the entry point and the target point than the second image;
determining at least one of a new entry point, a new guide member, a new target point, or combinations thereof when the displayed selected trajectory icon is not within the superimposed boundary icon;
displaying at least one of a new trajectory icon based on the new entry point, a new guide icon based on the new guide member, a new target point, or combinations thereof.

\* \* \* \* \*

UNITED STATES PATENT AND TRADEMARK OFFICE
CERTIFICATE OF CORRECTION

PATENT NO. : 11,842,030 B2
APPLICATION NO. : 15/420831
DATED : December 12, 2023
INVENTOR(S) : Matthew W. Koenig et al.

It is certified that error appears in the above-identified patent and that said Letters Patent is hereby corrected as shown below:

In the Specification

Column 3, Detailed Description, Line 34, Delete "40 and/or 102." and insert --42 and/or 102.-- therefor Column 4, Detailed Description, Line 13, Delete "124" and insert --120-- therefor Column 4, Detailed Description, Line 25, Delete "10," and insert --108,-- therefor Column 7, Detailed Description, Line 44, Delete "82." and insert --80.-- therefor Column 11, Detailed Description, Line 3, Delete "186" and insert --182-- therefor Column 11, Detailed Description, Line 8, Delete "186" and insert --182-- therefor Column 11, Detailed Description, Line 11, Delete "186" and insert --182-- therefor Column 11, Detailed Description, Line 17, Delete "124" and insert --120-- therefor Column 11, Detailed Description, Line 18, Delete "124" and insert --120-- therefor Column 11, Detailed Description, Line 19, Delete "124" and insert --120-- therefor Column 11, Detailed Description, Line 26, Delete "124," and insert --120,-- therefor Column 13, Detailed Description, Line 16, Delete "TRIM®," and insert --TRIA®,-- therefor Column 14, Detailed Description, Line 7, Delete "72944." and insert --294.-- therefor Signed and Sealed this
Twelfth Day of November, 2024

Katherine Kelly Vidal
*Director of the United States Patent and Trademark Office*

CERTIFICATE OF CORRECTION (continued)
U.S. Pat. No. 11,842,030 B2

Column 14, Detailed Description, Line 55, Delete "82." and insert --50.-- therefor Column 15, Detailed Description, Line 54, Delete "panning" and insert --planning-- therefor Column 17, Detailed Description, Line 7, Delete "316," and insert --360,-- therefor Column 17, Detailed Description, Line 32, Delete "124" and insert --120-- therefor Column 18, Detailed Description, Line 12, Delete "34" and insert --42-- therefor Column 18, Detailed Description, Line 14, Delete "353" and insert --354-- therefor Column 18, Detailed Description, Line 21, Delete "126" and insert --120-- therefor Column 18, Detailed Description, Line 27, Delete "116." and insert --166.-- therefor Column 18, Detailed Description, Line 40, Delete "126" and insert --120-- therefor